US010286364B2

(12) United States Patent
Tang et al.

(10) Patent No.: US 10,286,364 B2
(45) Date of Patent: May 14, 2019

(54) MIXED MATRIX MEMBRANES FOR OLEFIN/PARAFFIN SEPARATION AND METHOD OF MAKING THEREOF

(71) Applicant: BETTERGY CORP., Peekskill, NY (US)

(72) Inventors: Zhong Tang, Pompton Plains, NJ (US); Bo Lu, Croton on Hudson, NY (US); Xiaojuan Hu, Croton on Hudson, NY (US); Tuyen Pham, Camden, NJ (US); Lin-Feng Li, Croton on Hudson, NY (US)

(73) Assignee: BETTERGY CORP., Peekskill, NY (US)

( * ) Notice: Subject to any disclaimer, the term of this patent is extended or adjusted under 35 U.S.C. 154(b) by 31 days.

(21) Appl. No.: 15/482,942

(22) Filed: Apr. 10, 2017

(65) Prior Publication Data

US 2017/0291147 A1     Oct. 12, 2017

Related U.S. Application Data

(63) Continuation-in-part of application No. 14/705,100, filed on May 6, 2015, now Pat. No. 9,649,601.
(Continued)

(51) Int. Cl.
*B01D 53/22* (2006.01)
*B01D 63/10* (2006.01)
(Continued)

(52) U.S. Cl.
CPC .......... *B01D 71/68* (2013.01); *B01D 53/228* (2013.01); *B01D 67/0079* (2013.01);
(Continued)

(58) Field of Classification Search
CPC .. B01D 53/22; B01D 53/228; B01D 67/0079; B01D 69/04; B01D 69/08; B01D 69/148;
(Continued)

(56) References Cited

U.S. PATENT DOCUMENTS 4,740,219 A     4/1988  Kulprathipanja et al.
4,853,202 A *   8/1989  Kuznicki ................. B01J 29/89
                                                              423/326
(Continued)

OTHER PUBLICATIONS

A. F. Ismail et al., A Review on the Lates Development of Carbon Membranes for Gas Separation; Journal of Membrance Science 193 (2001) 1-18.
(Continued)

*Primary Examiner* — Jason M Greene
(74) *Attorney, Agent, or Firm* — Robert W. Morris; Eckert Seamans Cherin & Mellott, LLC

(57) ABSTRACT

The invention provides mixed matrix membranes (MMMs) for olefin/paraffin separation and methodes of making and using the same. The MMMs comprise a continuous polymer matrix with metal doped zeolite nano-particles. A separation technology based upon the composite membranes is effective for propylene and other olefin separation from olefin/paraffin mixtures, and the separation is more energy-efficient than the conventional cryogenic technique.

40 Claims, 2 Drawing Sheets

SEM image of MMM (Ag-ETS-10 zeolite with Polyimide polymer matrix)

Related U.S. Application Data

(60) Provisional application No. 62/320,779, filed on Apr. 11, 2016, provisional application No. 61/990,214, filed on May 8, 2014.

(51) Int. Cl.

| | | |
|---|---|---|
| *B01D 67/00* | (2006.01) | |
| *B01D 69/04* | (2006.01) | |
| *B01D 69/08* | (2006.01) | |
| *B01D 69/14* | (2006.01) | |
| *B01D 71/02* | (2006.01) | |
| *B01D 71/34* | (2006.01) | |
| *B01D 71/48* | (2006.01) | |
| *B01D 71/52* | (2006.01) | |
| *B01D 71/56* | (2006.01) | |
| *B01D 71/64* | (2006.01) | |
| *B01D 71/68* | (2006.01) | |
| *C07C 7/144* | (2006.01) | |

(52) U.S. Cl.
CPC ............ *B01D 69/04* (2013.01); *B01D 69/08* (2013.01); *B01D 69/148* (2013.01); *B01D 71/028* (2013.01); *B01D 71/34* (2013.01); *B01D 71/48* (2013.01); *B01D 71/52* (2013.01); *B01D 71/56* (2013.01); *B01D 71/64* (2013.01); *C07C 7/144* (2013.01); *B01D 63/10* (2013.01); *B01D 67/0016* (2013.01); *B01D 2256/24* (2013.01); *B01D 2257/702* (2013.01)

(58) Field of Classification Search
CPC .... B01D 71/022; B01D 71/028; B01D 71/26; B01D 71/34; B01D 71/48; B01D 71/52; B01D 71/56; B01D 71/64; B01D 71/68; B01D 2323/08; C07C 7/144
See application file for complete search history.

(56) References Cited

U.S. PATENT DOCUMENTS

| | | | |
|---|---|---|---|
| 4,938,989 A | 7/1990 | Steeves et al. | |
| 5,011,591 A | 4/1991 | Kuznicki | |
| 5,127,925 A * | 7/1992 | Kulprathipanja | B01D 53/22 95/138 |
| 6,414,202 B1 | 7/2002 | Baker et al. | |
| 6,500,233 B1 | 12/2002 | Miller et al. | |
| 6,525,236 B1 | 2/2003 | Baker et al. | |
| 7,109,140 B2 | 9/2006 | Marand et al. | |
| 7,166,146 B2 | 1/2007 | Miller et al. | |
| 7,479,227 B2 | 1/2009 | Da Costa et al. | |
| 8,017,825 B2 | 9/2011 | Kuznicki et al. | |
| 8,828,439 B2 | 9/2014 | Kuznicki | |
| 2003/0168407 A1* | 9/2003 | Kusakabe | B01D 53/228 210/650 |
| 2005/0014371 A1* | 1/2005 | Tsapatsis | B01D 67/0051 438/689 |
| 2006/0201884 A1* | 9/2006 | Kulprathipanja | B01D 71/028 210/651 |
| 2009/0270665 A1* | 10/2009 | Magalhaes Mendes | B01D 53/228 585/259 |
| 2010/0018926 A1* | 1/2010 | Liu | B01D 67/0079 210/655 |
| 2010/0143611 A1* | 6/2010 | Hutchinson | B01D 67/009 427/596 |
| 2010/0285190 A1* | 11/2010 | Sartorio | A23B 7/157 426/415 |
| 2012/0048109 A1* | 3/2012 | Chinn | B01D 53/228 95/130 |
| 2014/0231338 A1* | 8/2014 | Takaya | B01D 71/56 210/489 |
| 2015/0044130 A1* | 2/2015 | Tang | B01D 63/00 423/648.1 |
| 2017/0190640 A1* | 7/2017 | Noda | C07C 7/144 |

OTHER PUBLICATIONS

I. G. Giannakopoulos et al., Separation of Propylene/Propane Mixtures Using Faujasite-Type Zeolite Membranes; Ind. Eng. Chem. Res. 2005, 44, 226-230.

Zhang et al., High Performance ZIF8/6FDA-DAM Mixed Matrix Membrane for Propylene/Propane Separations; Journal of Membrance Science; 389 (2012) 34-42.

Paul et al., The Diffusion Time Lag in Polymer Membranes Containing Adsorptive Fillers; J. Polymer Sci.: Symposium No. 41, 79-93 (1973).

Ultrathin, Molecular-Sieving Graphene Oxide Membranes for Selective Hydrogen Separation; Hang Li et al.; Science 342, 95 (2013).

High Molecular Permeance in a Poreless Ceramic Membrane; Yunfeng Gu and S. Ted Oyama; Adv. Mater. 2007, 19, 1636-1640.

On-Stream Modification of MFI Zeolite Membranes for Enhancing Hydrogen Separation at High Temperature; Xuehong Gu, Zhong Tang and Junhang Dong; Microporous and Mesoporous Materials 111 (2008) 441-448.

\* cited by examiner

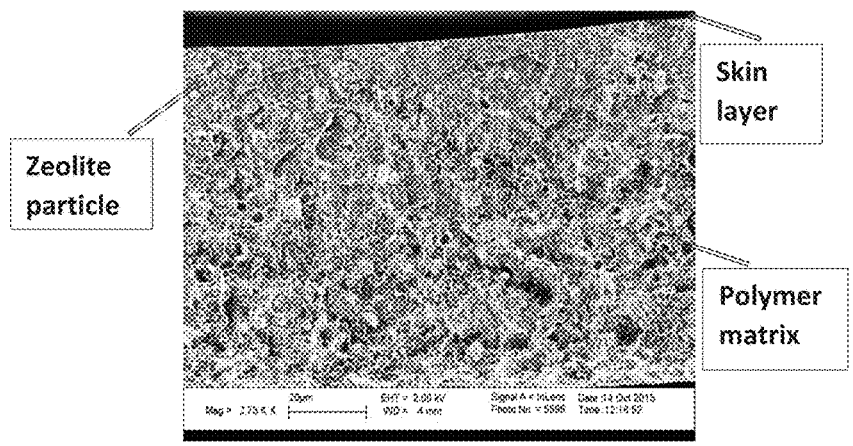
FIG. 1 - SEM image of MMM (Y zeolite with Polysulfone polymer matrix)
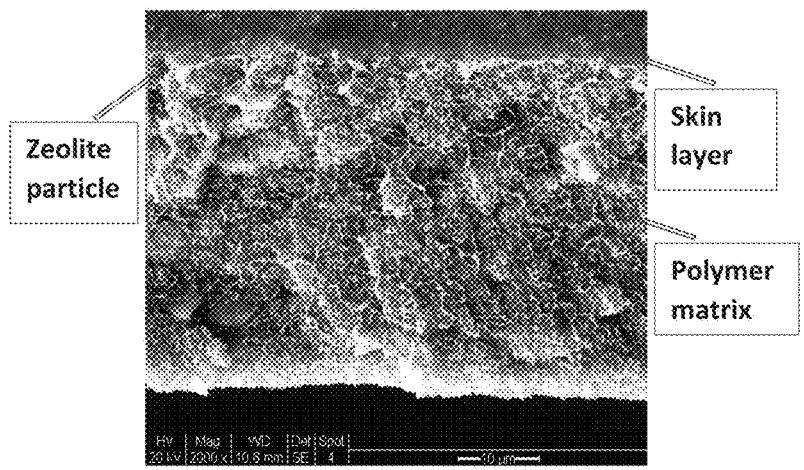
Fig. 2 - SEM image of MMM (Ag-ETS-10 zeolite with Polyimide polymer matrix)

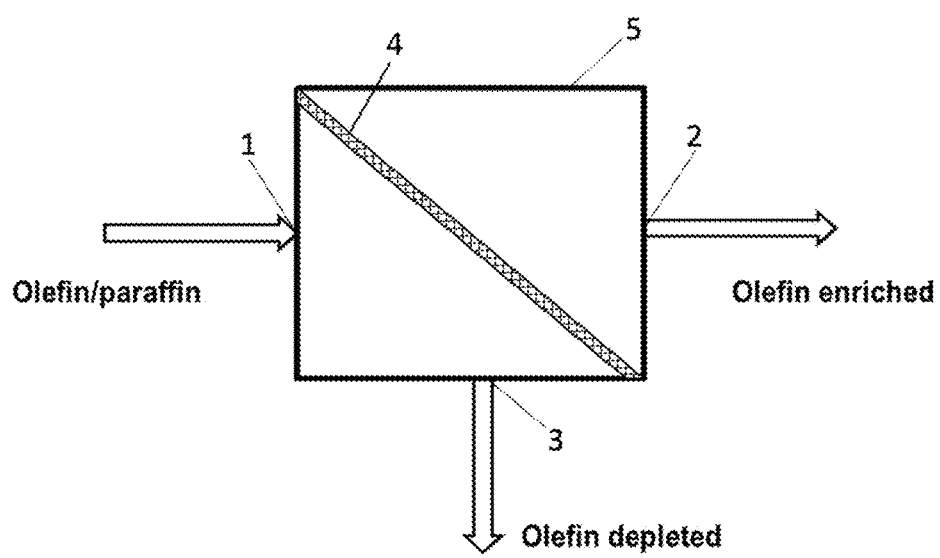
Fig. 3 – Membrane based apparatus for olefin separation

MIXED MATRIX MEMBRANES FOR OLEFIN/PARAFFIN SEPARATION AND METHOD OF MAKING THEREOF

CROSS-REFERENCE TO RELATED APPLICATIONS

This application is based upon, and claims the benefit of priority from, the U.S. patent application Ser. No. 14/705,100, filed May 6, 2015 (now U.S. Pat. No. 9,649,601), and its prior Provisional Application No. 61/990,214, filed May 8, 2014, as well as from the U.S. Provisional Application No. 62/320,779, filed Apr. 11, 2016. The disclosures of these applications are incorporated herein by reference in their entirety. In particular, the application Ser. No. 14/705,100 discloses apparatus for olefin separation from an olefin/paraffin mixture which comprises a membrane with a porous substrate and a zeolite layer thereon having pores with metal clusters in the zeolite pores.

STATEMENT REGARDING FEDERALLY SPONSORED RESEARCH OR DEVELOPMENT

The work described herein was partially supported by the United States Government under Grant Nos. IIP-1247577 and IIP-1430552, awarded by the U.S. National Science Foundation. The Federal Government may have certain rights in this invention.

BACKGROUND OF THE INVENTION

1. Field of the Invention

Membrane separation for olefin/paraffin mixtures offers an appealing energy-efficient alternative to the cryo-distillation process. Membranes have the potential to combine high selectivity with high permeability. Although substantial effort has been dedicated in developing a high flux, high selectivity olefin separation membrane, the state-of-the-art membrane cannot meet the stringent requirements of real life olefin/paraffin separation. Technical barriers include: (1) a trade-off between selectivity and flux; (2) poor stability especially under the practical operating environment; (3) fouling or poisoning in the presence of contaminants (olefins, alkynes, dienes, olefin sulfide, and other sulfur species); and (4) the high cost of producing the membranes. To commercialize the membrane separation technology on an industrial scale, a novel, robust olefin/paraffin separation membrane technology with large surface area, high flux and selectivity, excellent hydrothermal and chemical stability, and excellent durability under real operating conditions has to be developed.

This disclosure describes a new kind of mixed matrix membrane ("MMM") exhibiting high selectivity and flux that can be useful in cost-effective olefin/paraffin separation membrane technology. The membranes, made through a unique procedure, comprise at least one polymer matrix and at least one metal-doped zeolite material. This composite MMM is designed for gas separation in applications such as olefin purification from olefin/paraffin mixtures as the process streams in steam cracking plants, olefin recovery in the gas stream from oil fields and refinery plants, or the venting gas from polymerization plants.

2. Background Art

Membrane candidates have been proposed ranging from polymers, and ceramics, to the composites of them. Although polymeric membranes have been used successfully in several gas separation applications, including nitrogen production from air and olefin removal from refinery streams, the selectivity and gas fluxes of such membranes are inadequate for separating olefins from saturated hydrocarbons. Under industrial operating conditions, those polymeric membranes suffer from plasticization. Even the best polymeric membranes can only offer olefin/paraffin selectivity of 4-5. To replace or supplement distillation for the separation of olefin/paraffin in steam crackers or propane de-olefination plants, membranes with selectivity of twenty or more are needed.

Facilitated transport membranes have long been attracting research interest. Facilitated transport membranes incorporate a reactive carrier in the membrane which reacts with, and helps transport, one of the components of the feed across the membrane. High loadings (more than 80 wt % or 40 vol %) of silver salt ($AgBF_4$) as the carrier were normally used in the polymer membranes. Mixed-gas ethylene/ethane selectivity of more than 50 has been reported (U.S. Pat. Nos. 6,414,202; 6,525,236 and 7,479,227). The main hurdles, however, include the lack of carrier stability due to washout of silver ions, and the needs for water vapor in the feedstock. While complexing with olefins, the carriers also tend to react with other species causing undesirable carrier deactivation or poisoning over short time.

Inorganic membranes, such as carbon membranes (A. F. Ismail, L. I. B. David, *J. Membrane Sci.*, 2001, 193, 1-18) and zeolite membranes have also been investigated for the separation of olefin/paraffin gas mixtures. Inorganic membranes have much greater thermal and chemical stability. A few studies have indicated that zeolite membranes, specifically FAU (pore size 0.74 nm), and ETS-10 (pore size ~0.56 nm) zeolite membranes can separate olefin from paraffin. It has been reported that FAU-type zeolite membranes, synthesized by a secondary growth method, can reach a separation factor for propylene/propane mixtures of 13.7±1 at 100° C., with the corresponding propylene permeance of $0.75 \times 10^{-8}$ mol/m$^2$·s·Pa, which surpassed the performance of polymer membranes as well as carbon membranes (I. G. Giannakopoulos, V. Nikolakis, *Ind. Eng. Chem. Res.*, 2005, 44, 226-230). ETS-10 zeolite membranes have been reported to have a mixed coordination metallosilicate framework, with the formula $Na_2TiSi_5O_{13}$, discovered by Kuznicki at Engelhard (U.S. Pat. Nos. 4,938,989; 5,011,591). Silver ion exchanged ETS-10 zeolite powder has been reported to be adsorbent for noble gas adsorption (U.S. Pat. No. 8,828,439). Modified ETS-10 zeolite was also reported to be a good candidate to selectively adsorb ethylene over ethane (U.S. Pat. No. 8,017,825).

In summary, current membrane materials generally suffer from one or more of the following deficiencies: insufficient flux; low selectivity depending on the membrane material and application; instability when exposed to olefin, water, sulfur, or other contaminants; lack of high quality support material with uniform pore size and appropriate surface roughness; and inadequate long term testing under industrial conditions. The principal objective of the present invention intents to solve this challenging issue facing the industry.

It is known that olefins (e.g. ethylene and propylene) have a unique affinity to silver and silver ion (I) species. Silver-salt-based polymer membranes have higher olefin selectivity mainly through a facilitated transport mechanism. It is also known that zeolites possess excellent ion-exchange ability. By means of a silver ion-exchange, Ag can be introduced inside the pores of the zeolite membrane, which cannot only fine tune the pore size but also provide great selectivity toward ethylene. A metal-containing modified agent can passivate the external surface and control the opening size of the zeolite. The pore structure of zeolites can thus be modified by introducing new species through various techniques, such as ion exchange, impregnation, chemical vapor deposition or atomic layer deposition. Although zeolite membranes can be synthesized on a substrate, such as a porous disk or tube made from ceramic or metal, it is known that a high quality molecular sieve membrane is difficult to fabricate with good reproducibility because of the uncertainties of the several processes. Different from the molecular sieve powder synthesis, the inter-growth of the crystals during the secondary growth synthesis is difficult to control due to the random growth in a hydrothermal environment.

To address the issue of poor reproducibility, loss of mechanical strength in polymeric membranes and the high cost of production of molecular sieve membranes, mixed matrix membranes ("MMM") have been proposed. MMMs are composite membranes containing inorganic fillers embedded within the matrix of polymers. The presence of inorganic fillers within the polymers improves separation performance, mechanical strength and thermal stability of the polymeric membranes. MMM was reported as early as in 1970s (D. R. Paul, D. R. Kemp, *J. Polym Sci: Polym Phys.*, 1973, 41, 79-93). The concept of the MMM has been demonstrated at UOP LLC in the mid-1980s (U.S. Pat. Nos. 4,740,219; 5,127,925) using CA/silicalite MMMs for gas separation.

SUMMARY OF THE INVENTION

The present invention provides a new kind of MMM, which is composed of homogeneously interpenetrating inorganic particles in a polymer matrix. The MMMs made according to the invention are less costly to fabricate, while possessing excellent separation performance. These MMMs combine the advantages of both inorganic and polymeric membranes and are able to achieve higher selectivity, permeability, larger surface-area-to-volume ratio and mechanical integrity.

Inorganic materials such as molecular sieves, carbon molecular sieves and nano-metal oxides have been frequently used in the fabrication of MMMs for gas separation. (T. S. Chung, L. Y. Jiang, S. Kulprathipanja, *Prog. Polym Sci.*, 2007, 32, 483-507) Although such MMMs show potential selectivity for $CO_2/CH_4$, $H_2/CH_4$ and $O_2/N_2$ separation, little work has been done on propylene and propane separation. Koros, et al. investigated a ZIF-8/6FDA-DAM MMM for propylene and propane separation, with propylene/propane selectivity reaching about 22. (C. Zhang, Y. Dai, J. R. Johnson, O. Karvan, W. J. Koros, *J. Mem Sci.*, 2012, 389, 34-42) ZIF-8 is a metal organic framework made by zinc ions coordinated by four imidazolate rings. The problem with this material was that it is not stable during the long time operation at industrial conditions.

The present invention reports a new type of composite MMMs that uses molecular sieve nano-particles as the inorganic fillers, enabling the fabrication of MMMs for olefin separation.

BRIEF DESCRIPTION OF THE DRAWINGS

FIG. 1 is an SEM image showing a cross-section of Y zeolite dispersed in polysulfone matrix;

FIG. 2 is an SEM image showing a cross-section of Ag doped ETS-10 zeolite dispersed in polyimide matrix;

FIG. 3 is a representational diagram of a device for olefin/paraffin separation using a mixed matrix membrane;

DESCRIPTION OF THE PREFERRED EMBODIMENTS

1. Chemicals and Materials

The commercial available polymer resins, including poly sulfone (PS, Sigma Aldrich), polyether sulfone (PES, Sigma Aldrich), polyamide imide (Torlon®), poly imide (Matrimid® 5218) may be used for MMM membranes. The chemicals used in this work include potassium chloride (99.9%, Aldrich), potassium fluoride (99%, Aldrich), sodium chloride (99.9%, Aldrich), sodium hydroxide (99.9%, Aldrich), sodium silicate solution ($Na_2SiO_3$: 27% $SiO_2$, 8% $Na_2O$, Aldrich), and titania (P-25 anatase, Aldrich). The solvents to make the precursor include N-methyl-2-pyrrolidone (NMP), N,N-dimethylformamide (DMF), dimethyl sulfoxide (DMSO), and tetrahydrofuran (THF), all from Sigma-Aldrich. The propylene (99.5%), propane (CAS grade) gases were obtained from Airgas.

2. Preparation of Zeolite Nano-Particle Suspension

Y-type and MFI molecular sieves (with different Si/Al ratio) nano-particles were purchased from Alfa-Aesar. ETS-10 molecular sieve nanoparticles were prepared according to a specially designed procedure. An example of the ETS-10 molecular sieve synthesis is described here. 1.3 g potassium chloride, 6.9 g sodium chloride, and 1.5 g potassium fluoride were dissolved into 20.0 g distilled water. 20.0 g sodium silicate solution was added into the above mentioned solution, while keeping stirring at room temperature for at least 2 hours until forming a homogeneous solution. This solution was then mixed with a titanium source (1.3 g, anatase P-25) and diluted with another 40 ml DI water under stirring at room temperature for 3-4 hr. The precursor was transferred into a Teflon® cup fitted to an autoclave. The autoclave was placed in an oven for hydrothermal synthesis at 210° C. for 24 h. After cooling down to room temperature, the product was washed with the distilled water three times to obtain the nano-particles.

For the filler of MMMs preparation, the washed nano-particle suspension was centrifuged 3-4 times to collect the nano-particles. These nano-particles were then dried at 350° C. for 8 hours and ready for ion-exchange. Silver ion-exchange of the molecular sieve nano-particles was performed by putting ETS-10 molecular sieve nano-particles in an 0.2 M $AgNO_3$ solution at room temperature for 2 hours. The particles were then filtered and dried in an oven at 80° C. overnight. These dried particles were then subject to thermal treatment under a reforming gas (5% hydrogen balanced with nitrogen) with the following temperature program: at 100° C. for 1 h and then 350° C. for 8 h, with a heating rate of 1° C./min.

3. Preparation of Mixed Matrix Membranes

Mixed matrix membranes were prepared by the solvent-evaporation and phase-separation method. Inorganic fillers were the ion-exchanged molecular sieve nano-particles. Polymers used for the MMM's preparation can be any polymer resins. The following examples for the polymers used in this invention are, but not limited to, poly sulfone, polyether sulfone, poly polyamide imide, and polyimide.

General procedures for making MMMs are described as follows: 1) Making a metal-doped zeolite suspension in the solvent; 2) Dissolving a polymer in the suspension to become a precursor; 3) Casting the precursor on a glass plate, or spinning the precursor with spinneret; 4) Drying the cast or spun precursor in a vacuum and at a prescribed temperature (30-100° C.) for a prescribed time of 0.5-72 hr); 5) Immersing the dried precursor into water at a prescribed temperature (20-60° C.) for 10-60 min to form flat-sheet films or hollow fibers; 6) Drying the flat-sheet films or hollow fibers in a vacuum and at a prescribed temperature (30-50° C.) for a prescribed time (6-48 hr).

The membrane thickness can be controlled between 20-80 μm. The morphology of the membranes was characterized by a scanning electron microscope (SEM). The membrane integrity was observed using a SEM (LEO 1530VP FESEM-EDS).

4. EXAMPLES

Example I. Comparative Example for Membranes Consisting of Zeolite Without Metal Doping The following examples show the preparation of MMM membranes with polysulfone (PS) as the polymer matrix and a molecular sieve (zeolite) as the filler. Molecular sieve (Y-type, ZSM-5, and ETS-10, respectively) nano-particles were dispersed into an organic solvent (NMP), and stirred for 3 h to have an even dispersion of the particles. The solution was then mixed using a high speed mixer, degassed twice by ultrasonic means for 10 min each. The degassed solution was cast on a glass plate (with an applicator, space of 10 mil) and was slowly evaporated in a vacuum (0.1 bar) oven for 48 h. The film was then removed by soaking in water. The membrane film was further dried at 38° C. for 6 h, then 60° C. for 60 h, in a vacuum oven to remove the residual solvent and moisture. Different formulas of molecular sieve/PS membranes, with ratios of molecular sieve/polymer of 44.5/54.5, 45/55, 50.5/49.5 (wt %), were prepared.

Table 1 shows the relationship of the molecular sieve loading and the membrane permeance. The results show that the permeance increases with increasing molecular sieve loading. Higher percentages of molecular sieve in the formula (>46%) gave much larger gas permeability. It can also be seen that the MMMs made with non-doped zeolite nano-particles have negligible selectivity when separating a propylene/propane mixture.

TABLE 1

Performances of the prepared MMMs (#MMM-1-#MMM-4)

| Membrane No. | Zeolite type | Molecular sieve loading$^a$, (wt %) | PS in solvent$^b$, (wt %) | $C_3H_6$ permeance, (mol/m$^2$sPa) | $C_3H_6$/$C_3H_8$ selectivity |
|---|---|---|---|---|---|
| #MMM-1 | Y | 44.5 | 18 | $8.5 \times 10^{-9}$ | 1 |
| #MMM-2 | ZSM-5 | 45.0 | 18 | $2.7 \times 10^{-8}$ | 1 |
| #MMM-3 | ETS-10 | 45.0 | 20 | $1.8 \times 10^{-7}$ | 1 |
| #MMM-4 | ETS-10 | 50.5 | 20 | $2.4 \times 10^{-6}$ | 1 |

$^a$Z/(Z + P);
$^b$P/(P + N)
Z: Molecular sieve (weight),
P: Polysulfone (weight),
N: NMP (weight)

Example II. ETS-10 Zeolite Nano-Powders and Zeolite Metal Doping

This example shows the preparation procedure of ETS-10 nano-powders and the zeolite metal doping process. The ETS-10 molecular sieve synthesis is shown here. 1.3 g potassium chloride, 6.9 g sodium chloride, and 1.5 g potassium fluoride were dissolved into 20.0 g distilled water. 20.0 g sodium silicate solution was added into the above-mentioned solution, while stirring at room temperature for at least 2 hours until a homogeneous solution was formed. This solution was then mixed with a titanium source (1.3 g, anatase P-25) and diluted with another 40 ml DI water under stirring at room temperature for 3-4 hr. The precursor was transferred into a Teflon® cup fitted into an autoclave. The autoclave was placed in an oven for hydrothermal synthesis at 210° C. for 24 h. The synthesized slurry was washed with the distilled water three times to obtain the nano-particles.

Ion-exchange process was conducted over the powders by using silver nitrate solutions (0.125 N) to ensure a certain amount of Ag ions (doping in the zeolitic channels (MFI type), and ETS-10, or cages (Y-type). The particles were then filtered and dried in an oven at 80° C. overnight. These dried particles were then subject to thermal treatment with a reforming gas (5% hydrogen balanced with nitrogen) with a prescribed temperature program (at 100° C. for 1 h and 350° C. for 8 h, with a heating rate of 1° C./min).

Example III. #MMM-5 and #MMM-6 Membrane Preparation and Separation Performance These examples show the preparation procedure for MMM membranes with polyamide-imide (PAI) as the polymer matrix, and metal-doped Y zeolite powders, as well as their separation performance. Molecular sieve (Y-type) nano-particles were dispersed into organic solvent (NMP) and stirred for 3 h to have an even dispersion of the particles. Then 33% (wt) of the total amount of polymer was first added to the solution and stirred for 5 h to prevent the aggregation of molecular sieve particles. The remaining polymer (67% wt) was added and stirred for another 24 h to enhance the homogeneity. The solution was then mixed using a high speed mixer and degassed twice by ultrasonic means for 10 min each. The degassed solution was cast on glass plate (with an applicator, space of 10 mil, and 15 mil, respectively) and was slowly evaporated in a vacuum (0.1 bar) oven for 48 h. The film was removed by soaking in water. Finally, the membrane film was further dried at 38° C. for 6 h, then 60° C. for 60 h, in a vacuum oven to remove the residual solvent and moisture. The membrane's thickness could be controlled in between 60-120 μm. The separation experiment results listed in Table 2 show that the molecular sieve/PI MMMs had an olefin separation selectivity of 7.9, while the polymer membrane without the Y-type zeolite filler is dense with the permeate gas undetectable ($<1.0 \times 10^{-11}$ mol/m$^2$·s·Pa).

TABLE 2

Performances of the prepared MMMs (#MMM-5 and #MMM-6)

| Membrane No. | Ag doped Y (%) | Thickness (μm) | $C_3H_6$ permeance, (mol/m$^2$sPa) | $C_3H_6$/$C_3H_8$ selectivity |
|---|---|---|---|---|
| #MMM-5 | 0 | 53 | undetectable | n/a |
| #MMM-6 | 48 | 38 | $2.0 \times 10^{-10}$ | 7.9 |

Example IV. #MMM-7 and #MMM-8 Membrane Synthesis and Separation Performance

These examples show the preparation procedure for MMM membranes with polyimide (PI) as the polymer matrix and metal-doped ETS-10 zeolite powders. The separation performance of these membranes is shown in Table 3 below.

Molecular sieve (ETS-10) nano-particles were dispersed into organic solvent (NMP) and stirred for 3 h to have an even dispersion of the particles. Then 33% (wt) of the total amount of polymer was first added to the solution and stirred for 5 h to prevent the aggregation of molecular sieve particles. The remaining polymer (67% wt) was finally added and stirred for another 24 h to enhance the homogeneity. The solution was then mixed using a high speed mixer and degassed twice by ultrasonic means for 10 min each. The degassed solution was cast on a glass plate (with an applicator, space of 15 mil) and was slowly evaporated in a vacuum (0.1 bar) oven for 48 h. The film was then removed by soaking in water. Finally, the membrane film was further dried at 38° C. for 6 h, then 60° C. for 60 h, in a vacuum oven to remove the residual solvent and moisture. The membrane's thickness can be controlled in between 60-70 μm. The separation experiment results listed in Table 3 show that the molecular sieve/PI MMMs had an olefin separation selectivity of 20-30, and a propylene permeance of 0.5-0.7× $10^{-9}$ mol/m²·s·Pa.

TABLE 3

Performances of the prepared MMMs (#MMM-7 and #MMM-8)

| Membrane No. | Ag doped ETS-10 (%) | Thickness (μm) | $C_3H_6$ permeance, (mol/m²sPa) | $C_3H_6$/$C_3H_8$ selectivity |
|---|---|---|---|---|
| #MMM-7 | 48.5 | 66 | 0.59 × $10^{-9}$ | 30 |
| #MMM-8 | 49.3 | 68 | 0.67 × $10^{-9}$ | 25 |

Example V. #MMM-9 to #MMM-12 Membrane Synthesis and Separation Performance

These examples show the preparation procedure for MMM membranes with polyimide (PI) as the polymer matrix, and metal-doped ETS-10 zeolite powders. The separation performance of these membranes is shown in Table 4 below.

Molecular sieve (ETS-10) nano-particles were dispersed in an organic solvent (DMF or DMSO) and stirred for 3 h to have an even dispersion of the particles. Then 33% (wt) of the total amount of polymer was first added to the solution and stirred for 4 h to prevent the aggregation of molecular sieve particles. The remaining polymer (67% wt) was finally added and stirred for another 18 h to enhance the homogeneity. The solution was then mixed using a high speed mixer and degassed twice by ultrasonic means for 10 min each. The degassed solution was cast on a glass plate (with an applicator, space of 10 mil) and was slowly evaporated in a vacuum (0.1 bar) oven for 1-2 h. The film was then removed by soaking in water. Finally, the membrane film was further dried at 38° C. for 12 h in a vacuum oven to remove the residual solvent and moisture. The membrane's thickness can be controlled in between 40-50 μm. The separation experiment results listed in Table 4 show that the molecular sieve/PI MMMs had an olefin separation selectivity of 45-95, and a propylene permeance of 0.5-1.0× $10^{-9}$ mol/m²·s·Pa.

TABLE 4

Performances of the prepared MMMs (#MMM-9-#MMM-12)

| Membrane No. | Ag-ETS-10 (%) | Thickness (μm) | $C_3H_6$ permeance, (mol/m² · s · Pa) | $C_3H_6$/$C_3H_8$ selectivity |
|---|---|---|---|---|
| #MMM-9 | 49.4% | 52 | 0.89 × $10^{-9}$ | 45 |
| #MMM-10 | 49.0% | 48 | 0.72 × $10^{-9}$ | 71 |
| #MMM-11 | 48.5% | 47 | 0.62 × $10^{-9}$ | 95 |
| #MMM-12 | 47.8% | 49 | 0.53 × $10^{-9}$ | 82 |

As may be seen from Tables 2-4, the percentage of Ag doped zeolite is in the range of 47.8% to 49.4%.

FIG. 3 is a representational diagram of a device for olefin/paraffin separation using a mixed matrix membrane. FIG. 3 includes inlet 1, outlet 2, outlet 3, membrane 4, and chamber 5.

Inlet 1 allows for the injection of a stream, olefin/paraffin mixture. Upon injection of an olefin/paraffin mixture into chamber 5, the mixture passes through chamber 5 and reaches membrane 4. Membrane 4 has a relatively high selectivity for olefins in comparison to paraffins. As a result, olefin particles pass through membrane 4 and exit chamber 5 through outlet 2 in the form of an olefin enriched mixture. Conversely, membrane 4 has a relatively low selectivity for paraffins. As such, as olefins continue to pass through membrane 4, an olefin depleted mixture rich in paraffins will exit chamber 5 through outlet 3.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A mixed matrix membrane for use in separating olefins from an olefin/paraffin mixture, comprising particles of metal-doped molecular sieves dispersed in a matrix of polymeric material, wherein the molecular sieves comprise a zeolite forming a structure selected from the group consisting of ETS-type and Y-type, and wherein the structure comprises zeolite pores having metal clusters in the zeolite pores.

2. The mixed matrix membrane of claim 1, wherein the polymeric material is selected from the group consisting of poly sulfone, polyether sulfone, polystyrene, polyamide, polyimide, polyamide imide, polyketone, polyether ketone, polyether ether ketone, polyvinylidene fluoride, polyester, polybenzimidazole, polybenzobenzimidazole, and polybenzoxozole or mixture of them.

3. The mixed matrix membrane of claim 1, wherein the molecular sieves are selected from the group consisting of pure silicate molecular sieves, aluminosilicate molecular sieves, titanium silicate molecular sieves, and heteroatomic molecular sieves.

4. The mixed matrix membrane of claim 1, wherein the molecular sieves are doped with a metal selected from the group consisting of groups IB and VIII of the periodic table.

5. The mixed matrix membrane of claim 1, wherein the molecular sieves are doped with a metal selected from the group consisting of Ag, Cu, Pd, Pt, and alloys from them.

6. The mixed matrix membrane of claim 1, wherein the molecular sieves comprise a zeolite framework selected from the group consisting of FAU, FER, MFI, and MER.

7. The mixed matrix membrane of claim 1, wherein the molecular sieves comprise a zeolite selected from the group consisting of silicalite, aluminosilicate, and titanium silicalite.

8. The mixed matrix membrane of claim 1, wherein the molecular sieves comprise an ETS-type zeolite comprising a titania source selected from the group consisting of titanium (III) chloride, anatase, and titanium butoxide.

9. An apparatus for separating a mixture comprising an olefin and a paraffin, the apparatus comprising:
    a source of a stream which includes an olefin and a paraffin;
    a closed container body having an inlet coupled to said source, a first outlet for discharge of an olefin enriched stream, and a second outlet for discharge of an olefin depleted stream; and
    a mixed matrix membrane disposed in said body between said inlet and said first outlet, wherein the membrane comprises particles of metal-doped molecular sieves dispersed in a matrix of polymeric material, wherein the molecular sieves comprise a zeolite forming a structure selected from the group consisting of ETS-type and Y-type, and wherein the structure comprises zeolite pores having metal clusters in the zeolite pores.

10. The apparatus of claim 9, wherein the polymeric material is selected from the group consisting of poly sulfone, polyether sulfone, polystyrene, polyamide, polyimide, polyamide imide, polyketone, polyether ketone, polyether ether ketone, polyvinylidene fluoride, polyester, polybenzimidazole, polybenzobenzimidazole, and polybenzoxozole.

11. The apparatus of claim 9, wherein the mixed matrix membrane is in the form of at least one of:
    plate-and-frame;
    tubular;
    hollow-fiber bundler; and
    spiral wound module.

12. The apparatus of claim 9, wherein the molecular sieves are doped with a metal selected from the group consisting of groups IB and VIII of the periodic table.

13. The apparatus of claim 9, wherein the molecular sieves comprise a zeolite framework selected from the group consisting of at least one of FAU, FER, MFI, and MER.

14. The apparatus of claim 9, wherein the molecular sieves are selected from the group consisting of pure silicalite, aluminosilicate, titanium silicalite, and heteroatomic particles.

15. The apparatus of claim 9, wherein the molecular sieves comprise a zeolite selected from the group consisting of silicalite, aluminosilicate, and titanium silicalite.

16. The apparatus of claim 9, wherein the molecular sieves comprise an ETS-type zeolite having a titania source selected from the group consisting of titanium (III) chloride, anatase, and titanium butoxide.

17. A method of forming a mixed matrix membrane, comprising the steps of:
    suspending a metal-doped molecular sieve in a solvent to form a suspension, said molecular sieve comprising a zeolite forming a structure selected from the group consisting of ETS-type and Y-type, and wherein the structure comprises zeolite pores having metal clusters in the zeolite pores:
    dissolving a polymer into the suspension to form a precursor;
    at least one of:
        casting the precursor onto a plate; and
        spinning the precursor;
    drying the precursor in a vacuum at a predetermined temperature for a predetermined time;
        immerging the dried precursor into water to form at least one of:
        flat sheets; and
        hollow fibers;
    drying the at least one of flat sheets and hollow fibers in a vacuum at a predetermined temperature for a predetermined time; and
    subjecting the at least one of flat sheets and hollow fibers to at least one of vapor deposition and plasma treatment.

18. The method of claim 17, wherein the polymer is selected from a group consisting of poly sulfone, polyether sulfone, polystyrene, polyamide, polyimide, polyamide imide, polyketone, polyether ketone, polyether ether ketone, polyvinylidene fluoride, polyester, polybenzimidazole, polybenzobenzimidazole, and polybenzoxozole or mixture of them.

19. The method of claim 17, wherein the solvent is selected from the group consisting of:
    N-methyl-2-pyrrolidone;
    N,N-dimethylformamide;
    dimethyl sulfoxide; and
    tetrahydrofuran.

20. The method of claim 17, wherein the step of drying the precursor comprises drying the precursor in a vacuum at a temperature between thirty degrees Celsius and one hundred degrees Celsius for at least thirty minutes.

21. The method of claim 17, wherein the step of immerging comprises immerging the dried precursor into water at a temperature between twenty degrees Celsius and sixty degrees Celsius for at least ten minutes.

22. The method of claim 17, wherein the step of drying the at least one of flat sheets and hollow fibers in a vacuum comprises drying the at least one of flat sheets and hollow fibers in a vacuum at a temperature between thirty degrees Celsius and fifty degrees Celsius.

23. The method of claim 17, wherein the metal-doped molecular sieve is doped with a metal selected from a group consisting of groups IB and VIII of the periodic table.

24. The method of claim 17, wherein the metal-doped molecular sieve is doped with a metal selected from a group consisting of Ag, Cu, Pd, Pt, and alloys from them.

25. The method of claim 17, wherein the molecular sieve comprises a zeolite framework selected from the group consisting of FAU, FER, MFI, and MER.

26. The method of claim 17, wherein the molecular sieve is selected from the group consisting of pure silicate molecular sieves, aluminosilicate molecular sieves, titanium silicate molecular sieves, and heteroatomic molecular sieves.

27. The method of claim 17, wherein the molecular sieve comprises an ETS-type zeolite comprising a titania source selected from the group consisting of titanium (III) chloride, anatase, and titanium butoxide.

28. The mixed matrix membrane of claim 4, wherein the metal clusters comprise the selected metal.

29. The mixed matrix membrane of claim 5, wherein the metal clusters comprise the selected metal.

30. The apparatus defined in claim 12, wherein the metal clusters comprise the selected metal.

31. The method defined in claim 23, wherein the metal clusters comprise the selected metal.

32. The method defined in claim 24, wherein the metal clusters comprise the selected metal.

33. The mixed matrix membrane of claim 1, wherein the molecular sieves are doped with Ag to provide a weight range of 47.8% to 49.4% of Ag doped zeolite in the mixed matrix membrane.

34. The apparatus of claim 9, wherein the molecular sieves are doped with Ag to provide a weight range of 47.8% to 49.4% of Ag doped zeolite in the mixed matrix membrane.

35. The method of claim 17, wherein the molecular sieves are doped with Ag to provide a weight range of 47.8% to 49.4% of Ag doped zeolite in the mixed matrix membrane.

36. The method of claim 17, further subjecting the at least one of flat sheets and hollow fibers to at least one of temperature programmed reduction, temperature programmed calcination, and ultraviolet radiation.

37. The mixed matrix membrane of claim 4, wherein metal doping of the molecular sieves is achieved by at least one of vapor deposition and plasma treatment.

38. The mixed matrix membrane of claim 37, wherein the molecular sieves are subjected to additional treatment selected from the group consisting of temperature programmed reduction, temperature programmed calcination, and ultraviolet radiation.

39. The mixed matrix membrane of claim 5, wherein metal doping of the molecular sieves is achieved by at least one of vapor deposition and plasma treatment.

40. The mixed matrix membrane of claim 39, wherein the molecular sieves are subjected to additional treatment selected from the group consisting of temperature programmed reduction, temperature programmed calcination, and ultraviolet radiation.

* * * * *